(12) United States Patent
Whitaker (10) Patent No.: US 7,715,590 B2
(45) Date of Patent: May 11, 2010

(54) REAL-TIME IMAGE DETECTION USING POLARIZATION DATA

(75) Inventor: Sheila G. Whitaker, Gurley, AL (US)

(73) Assignee: Intergraph Technologies Company, Las Vegas, NV (US)

( * ) Notice: Subject to any disclaimer, the term of this patent is extended or adjusted under 35 U.S.C. 154(b) by 1130 days.

(21) Appl. No.: 11/344,971

(22) Filed: Feb. 1, 2006

(65) Prior Publication Data

US 2006/0215879 A1 Sep. 28, 2006

Related U.S. Application Data

(60) Provisional application No. 60/649,260, filed on Feb. 2, 2005.

(51) Int. Cl.
*G06K 9/00* (2006.01)
*G02B 27/28* (2006.01)

(52) U.S. Cl. ................... 382/103; 382/169; 359/483

(58) Field of Classification Search ............ 382/103, 382/106, 108, 112–123, 140, 154, 162, 168, 382/180, 181, 189, 193–195, 209, 232, 274, 382/276, 282, 295, 305, 318–321, 169, 170; 235/487; 340/10.1; 250/208.1, 338.1; 356/369; 359/483; 380/54
See application file for complete search history.

(56) References Cited

U.S. PATENT DOCUMENTS 5,483,066 A * 1/1996 Sadjadi et al. .......... 250/338.1
5,519,200 A * 5/1996 Williams .................. 235/487
6,075,235 A * 6/2000 Chun ...................... 250/208.1
6,301,044 B1 * 10/2001 Huber et al. ............... 359/483
7,049,933 B1 * 5/2006 Koerner ..................... 340/10.1
7,162,035 B1 * 1/2007 Durst et al. ................. 380/54
7,289,211 B1 * 10/2007 Walsh et al. ............... 356/369
2002/0181761 A1 12/2002 Barbour .................... 382/154
2003/0103214 A1 6/2003 VanDelden ................ 356/491

OTHER PUBLICATIONS

L.J. Denes et al., Spectro-Polarimetric Imaging for Object Recognition, 1998.
International Search Report dated Jul. 7, 2006.
Denes et al., A Spectro-Polarimetric Imager for Scene Discrimination, ISSSR '97 Paper, (1992).
Jiao et al., Depth-resolved two-dimensional Stokes vectors of backscattered light and Mueller matrices of biological tissue measured with optical coherence tomography, vol. 39, No. 34, (2000).

* cited by examiner

*Primary Examiner*—Seyed Azarian
(74) *Attorney, Agent, or Firm*—Sunstein Kann Murphy & Timbers LLP (57) ABSTRACT

The present invention relates to a system and method of detecting polarized identification indicia in real-time. A frame of image data is provided having a plurality of pixels, wherein each pixel includes polarized light intensity information. An intensity value is determined for each of the pixels from the polarized light intensity information. A first portion of the pixels having intensity values within an intensity range is selected. The pixels in the first portion having similar angle of linear polarization values within a tolerance range are analyzed, thereby detecting the polarized identification indicia in the image data.

32 Claims, 4 Drawing Sheets

FIG. 6

REAL-TIME IMAGE DETECTION USING POLARIZATION DATA

CROSS-REFERENCE TO RELATED APPLICATIONS

This patent application claims priority under 35 U.S.C. §119(e) to U.S. Provisional Patent Application No. 60/649,260, filed Feb. 2, 2005, entitled REAL-TIME MARKINGS DETECTION USING POLARIZATION DATA IN VIDEO IMAGES, which is incorporated by reference herein.

FIELD OF THE INVENTION

The invention generally relates to image detection and, more particularly, the invention relates to detecting polarized identification indicia in real-time.

BACKGROUND OF THE INVENTION

Polarizing materials that absorb light waves at differing angles may be used to discriminate areas of interest. For example, light reflected or emitted from man-made objects often differs from natural objects in its polarization state. Accordingly, such reflected light may be used to detect polarized identification indicia, e.g., identification badges. Some prior art techniques are capable of reading polarized image data while at the same time being incapable of interpreting the meaning of such data in real-time.

SUMMARY OF THE INVENTION

In general, in one aspect, the invention features a method of detecting polarized identification indicia in real-time. The method includes providing a frame of image data having a plurality of pixels, wherein each pixel includes polarized light intensity information, determining an intensity value for each of the pixels from the polarized light intensity information, selecting a first portion of the pixels having intensity values within an intensity range, and analyzing the pixels in the first portion having similar angle of linear polarization values within a tolerance range, thereby detecting the polarized identification indicia in the image data.

In general, in another aspect, the invention features a method of detecting polarized identification indicia in real-time. The method includes providing a frame of image data having a plurality of pixels, wherein each pixel includes polarized light intensity information, determining an intensity value for each of the pixels from the polarized light intensity information, selecting a first portion of the pixels having intensity values within an intensity range, determining a degree of linear polarization value for each of the pixels in the first portion, selecting a second portion of the pixels from the first portion, the second portion having degree of linear polarization values within a degree of linear polarization range, and analyzing the pixels in the second portion having similar angle of linear polarization values within a tolerance range, thereby detecting the polarized identification indicia in the image data.

In general, in another aspect, the invention features a computer program product for detecting polarized identification indicia in real-time. The computer program product includes a computer usable medium having computer readable program code thereon, the computer readable program code having program code for determining an intensity value for image data having a plurality of pixels, wherein each pixel includes polarized light intensity information, program code for selecting a first portion of the pixels having intensity values within an intensity range, and program code for analyzing the pixels in the first portion having angle of linear polarization values within a tolerance range, thereby detecting the polarized identification indicia in the image data.

In general, in another aspect, the invention features a system of detecting polarized identification indicia in real-time. The system includes an image device for receiving a frame of image data having a plurality of pixels, wherein each pixel includes polarized light intensity information and an image processor for determining an intensity value for each of the pixels from the polarized light intensity information, selecting a first portion of the pixels having intensity values within an intensity range, and analyzing the pixels in the first portion having similar angle of linear polarization values within a tolerance range, thereby detecting the polarized identification indicia in the image data.

BRIEF DESCRIPTION OF THE DRAWINGS

The foregoing and advantages of the invention will be appreciated more fully from the following further description thereof with reference to the accompanying drawings wherein.

DESCRIPTION OF ILLUSTRATIVE EMBODIMENTS

Various embodiments of the present invention relate to a system and method for detecting polarized identification indicia in real-time. To those ends, the concepts described herein define an approach for analyzing image data that has identification indicia present having a unique polarization signature. In one embodiment, the data detecting concept is unique in the use of intensity as a culling criterion and its real-time manipulation of a video stream. Other embodiments may use other culling criteria. Illustrative embodiments analyze frames of image data, remove areas not demonstrating predetermined polarized characteristics and may further enhance areas of interest. The polarized materials may be arranged in such a manner as to develop a coding mechanism that is undetectable to the human eye. The processed data may be passed to an output device for viewing or recording. Other routines may process the image data either prior to or after the detection routine.

Figure 1:
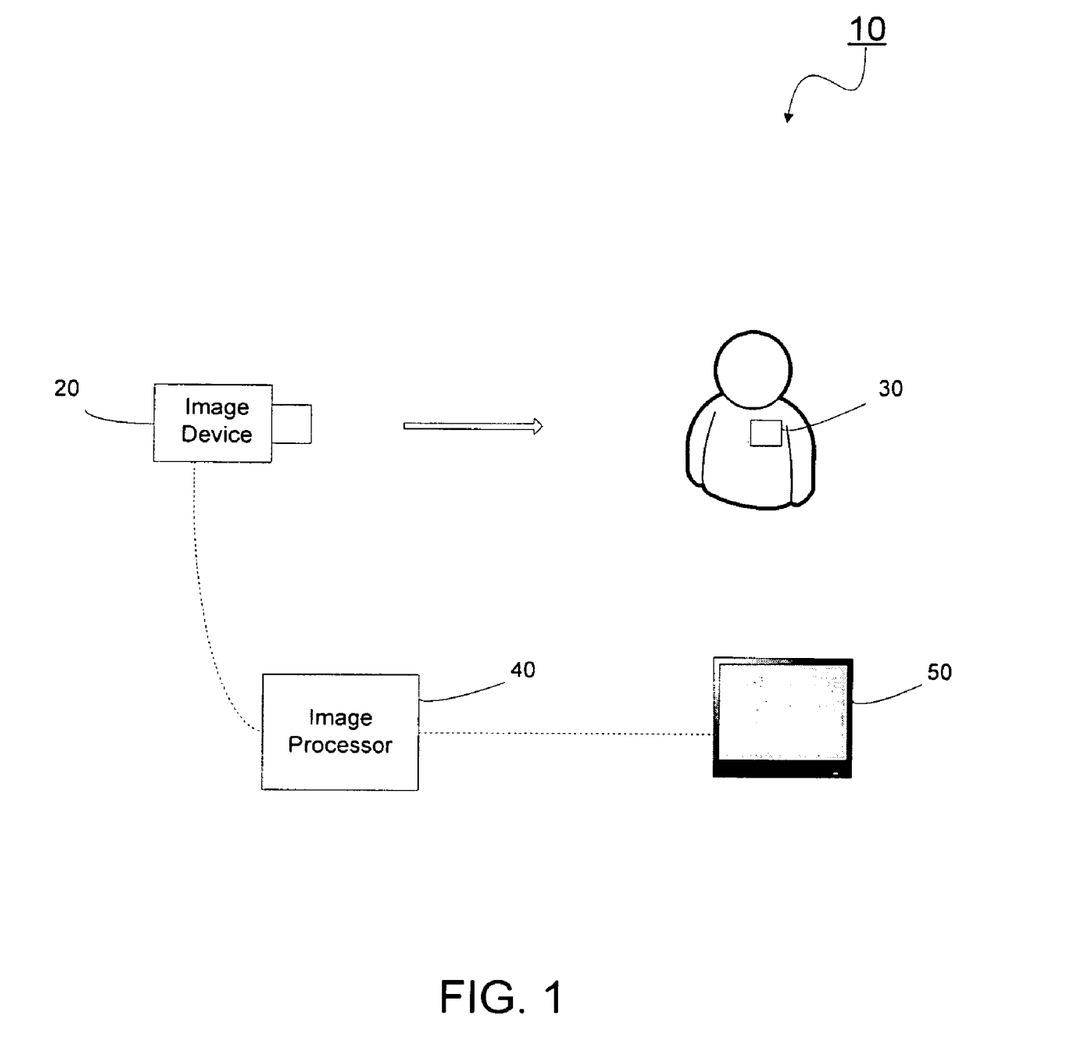
FIG. 1 shows a system of detecting polarized identification indicia in real-time according to an embodiment of the present invention.

FIG. 1 shows a system for detecting polarized identification indicia in real-time according to an embodiment of the present invention. The system 10 includes an image device 20 which captures polarized identification indicia 30 within an image and an image processor 40 that analyzes the image data received from the image device 20 and detects the identification indicia 30 in real-time. The processed image data may be passed to an output device 50 for further processing or displaying the detected identification indicia 30. The image device 20 may be a video device or a camera having filters or polarizers capable of capturing polarized light intensity information. The system 10 is capable of detecting polarized identification indicia 30 that is stationary such as a sign or moving such as a vehicle with indicia on it or a moving person wearing a badge. The polarized identification indicia 30 may be made from any polarizing material or materials. The image processor 40 may be capable of analyzing the image data and detecting the identification indicia 30 in real-time. For example, an image processor receiving up to 30 frames/second of data may be capable of processing and detecting the identification indicia 30 with a delay of only about 4 frames.

Figure 2:
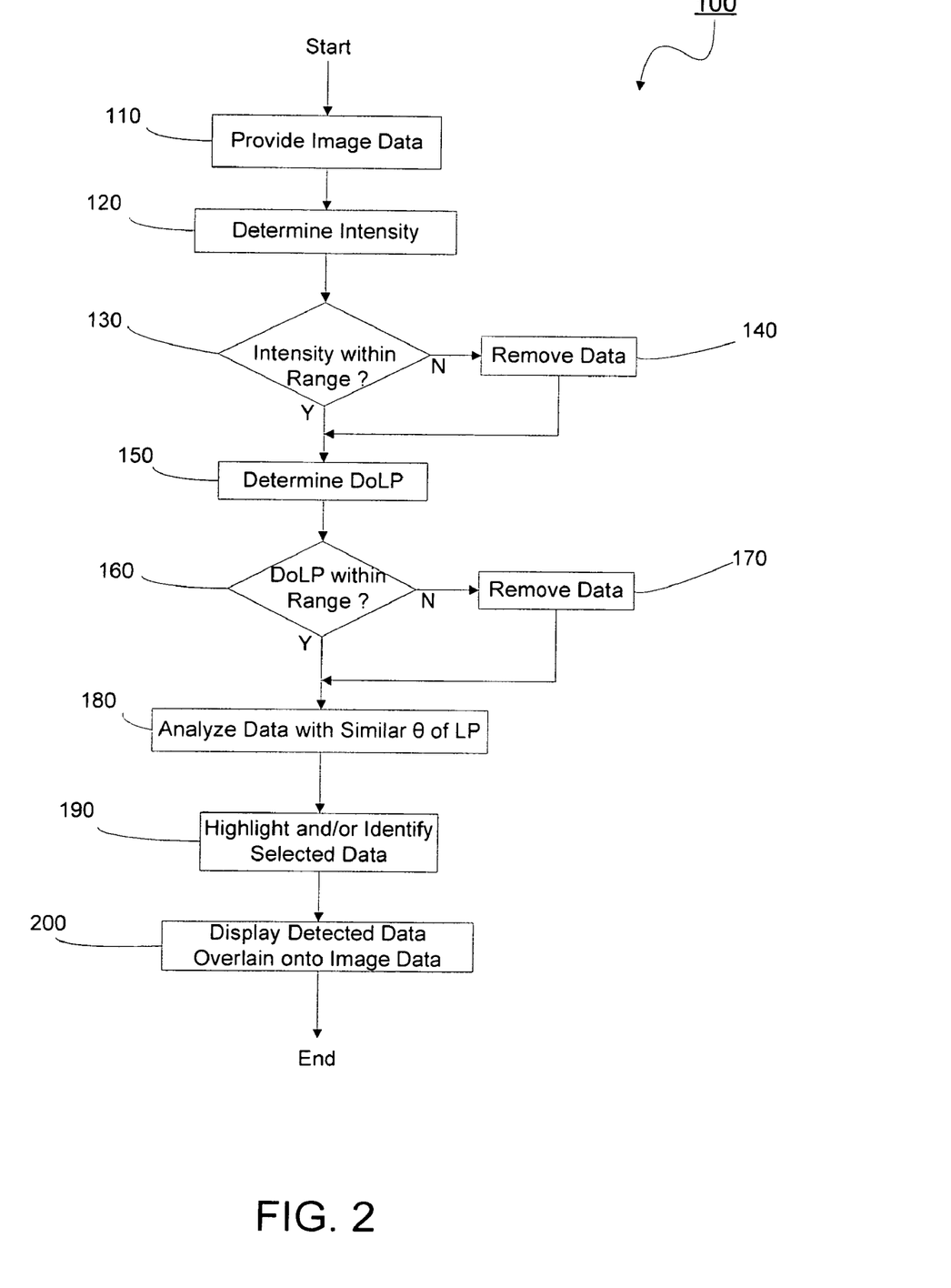
FIG. 2 shows a method of detecting polarized identification indicia in real-time according to an embodiment of the present invention.

FIG. 2 shows a method of detecting polarized identification indicia in real-time 100 according to an embodiment of the present invention. In step 110, image data having polarized light intensity information is provided. Among other things, the image data may be a previously captured image or an image received from a streaming device. For example, the image data may be a video image processed directly from a camera stream. The camera may use a lens with three linear polarization filters, such as filters at 0°, 45° and 90° to the camera axis, to capture the individual data components. For instance, each pixel value within the image may contain polarized light intensity information $I_0$, $I_{45}$, and $I_{90}$ scaled to the RGB range of 0 to 255. Other configurations may be used to provide polarized light intensity information as will be apparent to those of ordinary skill in the art. For example, one linear polarizer may be rotated to three angular positions in front of a single detector or three separate polarizing elements may be positioned in different orientations on three separate image detectors.

The polarized light intensity information may be used to calculate a Stokes vector. The Stokes vector was developed by George Stokes to describe polarized light with four quantities.

$$S = \begin{vmatrix} S_0 \\ S_1 \\ S_2 \\ S_3 \end{vmatrix} = \begin{vmatrix} 2I_0 \\ 2I_1 - 2I_0 \\ 2I_2 - 2I_0 \\ 2I_3 - 2I_0 \end{vmatrix} \quad (1)$$

$S_0$=Intensity of the incident beam.
$S_1$=Tendency of light to be horizontal or vertically polarized
$S_2$=Tendency of be linearly polarized at 45°
$S_3$=Tendency of light to be circularly polarized
In illustrative embodiments, $S_3$ is not required.
In polarimetry, the Stokes Vector S is populated with data from different polarization analyzers in front of a detector as $$S = \begin{vmatrix} S_0 \\ S_1 \\ S_2 \end{vmatrix} = \begin{vmatrix} I_H + I_V \\ I_H - I_V \\ 2I_{45} - (I_H + I_V) \end{vmatrix} \quad (2)$$

In equation 2 above, $I_H$, $I_V$ and $I_{45}$ are the light intensities measured at horizontal linear polarization 0°, vertical linear polarization 90°, and 45° linear polarization, respectively, relative to the camera's vertical viewing axis. Performing simple substitution, the Stokes vector is derived below:

$$S = \begin{vmatrix} S_0 \\ S_1 \\ S_2 \end{vmatrix} \begin{vmatrix} I_H + I_V \\ 2I_H - I_H - I_V \\ 2I_{45} - I_H - I_V \end{vmatrix} = \begin{vmatrix} I_H + I_V \\ I_H - I_V \\ 2I_{45} - I_H - I_V \end{vmatrix} \quad (3)$$

From the Stokes vector, the degrees of linear polarization (DoLP), the angle of linear polarization (θ), and Intensity (I) are derived as follows:

$$I \text{ corresponds to the total intensity} = S_0 \approx 2I_0. \quad (4)$$

$$DoLP = \frac{\sqrt{S_1^2 + S_2^2}}{S_0}, \quad (5)$$

$$\theta = -\frac{1}{2} a \tan\left(\frac{S_2}{S_1}\right) \quad (6)$$

Although the Stokes vector is derived above using horizontal, vertical and 45° linearly polarized components in image data, the Stokes vector may be calculated using other polarized light intensity information as will be apparent to those of ordinary skill in the art. For example, light may be measured without polarization filters and with a vertical linear polarizer, a +45° linear polarizer and a right-hand or left-hand circular polarizer to calculate the Stokes vector.

The Stokes vector varies in relation to the angle of light incident on a given object. Light incident on linearly polarized materials will reflect linearly polarized light having an intensity that is relatively "consistent" for a given material. Hence, polarized materials may maintain similar Intensity values, allowing Intensity to be used to differentiate between materials.

In step 120, image data may be processed to determine an Intensity value for each pixel within the image from the polarized light intensity information. In step 130, an intensity range may be specified so that the Intensity may be used as a criteria to cull or remove unwanted image data. For instance, a user may specify an intensity range depending on the identification indicia material used. For example, the Intensity may be selected to have a range from about 4% to about 98%. In step 140, areas that exceed desired levels of Intensity or that are outside of specified ranges may be removed. For example, data with little Intensity information may be removed, e.g., on the RGB scale of 0-255, values from 0 to about 15. The remaining image data may be used to calculate the Stokes Vector ($S_0$, $S_1$, and $S_2$), obtain DoLP values and/or obtain θ values from the polarized light intensity information.

In step 150, the image data within the specified intensity range may be further processed to determine a DoLP value for the selected pixels in the image. In step 160, a degree of linear polarization range may be specified for the values. For instance, a user may specify a degree of linear polarization range depending on the identification indicia material used since the material may demonstrate different polarization signatures. For example, the degree of linear polarization may be selected to have a range of 0.3 to 1.0. In step 170, areas that exceed desired levels of DoLP or that are outside of specified ranges may be removed. In one embodiment, step 130 and step 160 may be combined and data not falling within the selected intensity range and the DoLP range may be removed.

After removing or culling areas outside of specified criteria, the remaining data is analyzed for regions or points that maintain similar θ values within a specified error tolerance (step 180). Regions having a similar θ value within a specified error tolerance may be grouped together and selected for further processing. For example, for a nominal θ value of 10 degrees with an error tolerance of 9 on a scale of 0 to 100, data having a θ value of from about 9.1 degrees to about 10.9 degrees may be gathered into one group or bin. Points or pixels with similar θ values may also be analyzed to determine whether the distance from one another is outside of a specified distance range. For example, the distance between pixels having similar θ values may be selected to be no greater than 5 to 6 pixels away or apart. If the distance between the pixels is beyond the specified range, then the points may not be grouped together.

The data may be analyzed for any number of θ values and gathered into one or more groups or bins relative to their similar θ values and distance to one another, each group having a similar θ value within the specified error tolerance. The data within a group may be further analyzed to determine whether the data meets a specified size requirement. For instance, the size (width and height) of the region or the amount of data needed for an object to be detected may be defined within a specified size range. For example, data may be selected to be a minimum of 9 pixels in width and 6 pixels in height in order to be detected. Regions that are analyzed and grouped but that do not constitute enough data to represent the polarized identification indicia or a portion thereof, may continue to be grouped or may be discarded.

In step 190, the image data in a group or bin may be highlighted, used as a template or code to identify the polarized identification indicia, or both. For instance, the image data in a group or bin having similar θ values may be assigned a unique, individual code, such as a digit or symbol. For example, an image may have one region detected with one θ value, where a value of "0" is assigned to that group and two other regions detected with a different θ value, where a value of "1" is assigned to both of those groups. The minimum number of code elements needed to identify an object may be defined or selected. The code elements may be further analyzed for data content and used to identify the polarized identification indicia, e.g., from characteristics of the code in relation to objects with those characteristics. For instance, the code elements may be compared to a database of polarization signatures and the identification indicia identified. For example, cargo could be vendor coded and the vendor's ID mapped to the coded value similar to a bar code's use in identifying products.

In one embodiment, the highlighted image data in a group or bin may be assigned a color so that the detected area appears more noticeable or distinctive when viewing the image. In step 200, the highlighted area, the identified area, or both may then be overlain onto the original image for further processing of the image or to illustrate correctness of the detection routine. Although various ranges have been discussed above for the selecting criteria, it will be apparent to those skilled in the art that other ranges may be used depending on a number of factors, such as the polarizing material used, the size of the indicia and the application.

Figure 3:
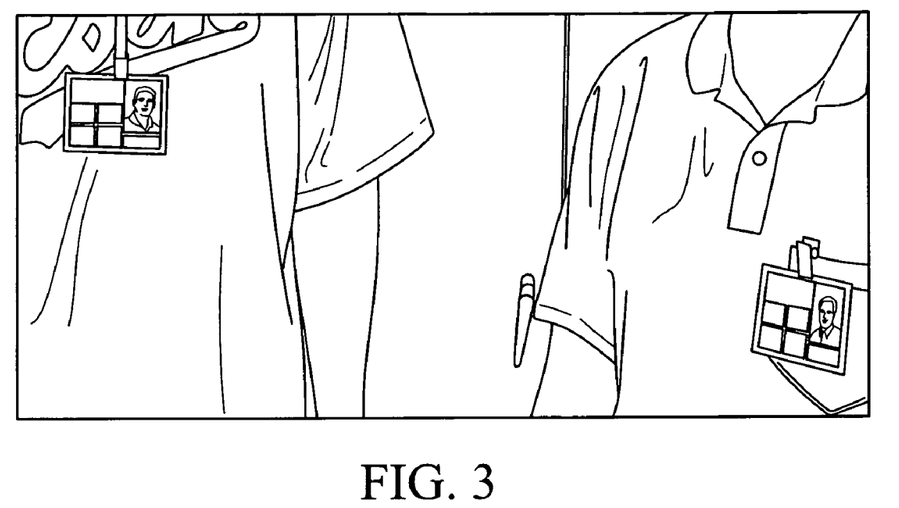
FIG. 3 schematically shows an image with polarized identification indicia present.

For illustration purposes, FIG. 3 depicts two individuals each wearing identification badges containing polarizing identification material with differing polarization signatures. As shown, the polarizing identification indicia is not distinguishable from other parts of the badge when viewed by an image device such as the human eye.

Figure 4:
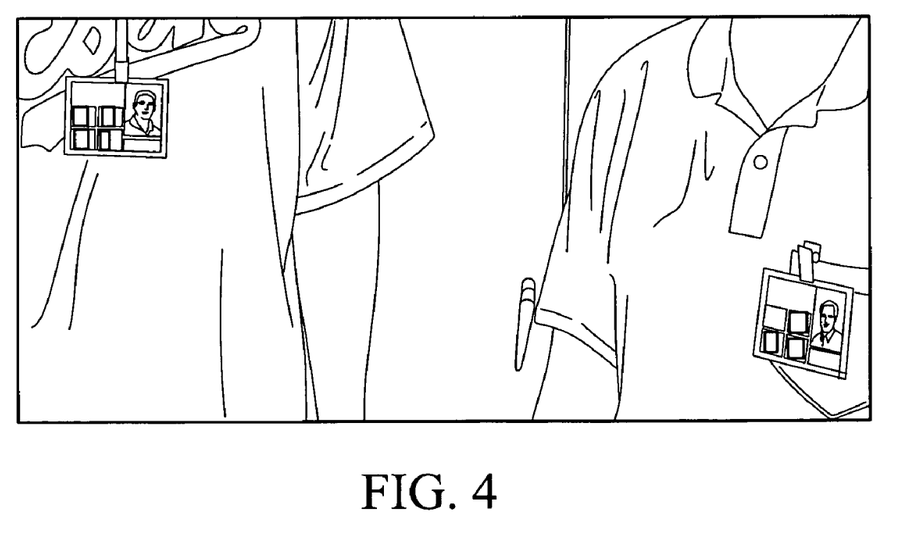
FIG. 4 schematically shows an image with polarized identification indicia detected according to an embodiment of the present invention.
Figure 5:
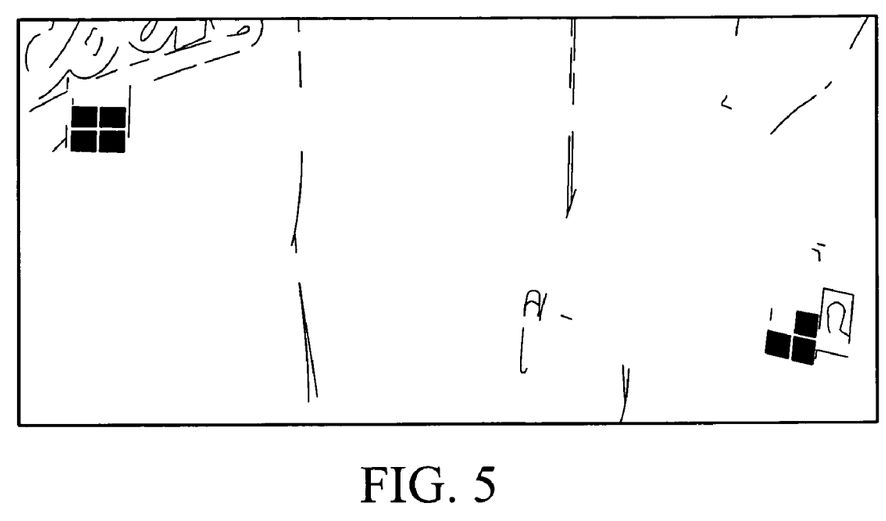
FIG. 5 schematically shows a culled image with polarized identification indicia selected according to an embodiment of the present invention.
Figure 6:
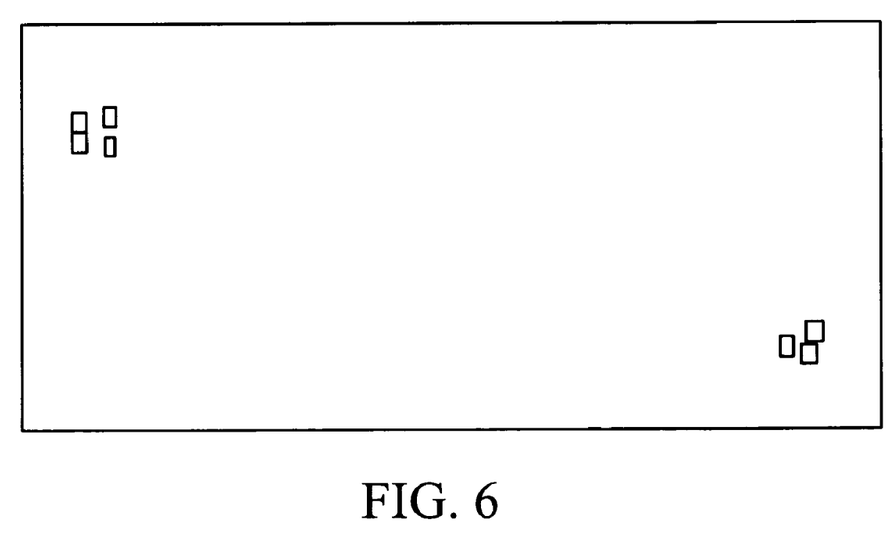
FIG. 6 schematically shows an image with polarized identification indicia highlighted according to an embodiment of the present invention.

As shown by FIG. 4, polarized identification indicia have been detected and the highlighted, detected areas are overlain onto the original image. The squares indicate the areas have been grouped or binned together due to the data similarities. The squares on each badge have a common color indicating that these areas have been gathered into groups or bins with similar θ values, e.g., the squares on one badge are green and on the other badge are purple. The detected areas constitute polarized identification indicia, e.g., a badge, due to their θ, proximity and size relative to selection criteria. The data within the highlighted areas may be further analyzed to determine the corresponding badge owner by the characteristics of the data and those defined for the badge. FIG. 5 illustrates the after effect of data culling. Selected areas have been culled or removed as data of non-interest based on the selection criteria. FIG. 6 illustrates just the overlay portion of the data indicating that the detected areas have been highlighted with two different colors, purple (shown on the left) and green (shown on the right).

Various embodiments of the invention may be implemented at least in part in any conventional computer programming language. For example, some embodiments may be implemented in a procedural programming language (e.g., "C"), or in an object oriented programming language (e.g., "C++"). Other embodiments of the invention may be implemented as preprogrammed hardware elements (e.g., application specific integrated circuits, FPGAs, and digital signal processors), or other related components.

In one embodiment, the disclosed apparatus and methods may be implemented as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., WIFI, microwave, infrared or other transmission techniques). The series of computer instructions may embody all or part of the functionality previously described herein with respect to the methods. For example, the computer readable program code may include instructions for determining an intensity value for image data having polarized light intensity information, for selecting data having intensity values within an intensity range and for analyzing the image data having angle of linear polarization values within a tolerance range, thereby detecting the polarized identification indicia in the image data.

Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies.

Among other ways, such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software.

Although the above discussion discloses various exemplary embodiments of the invention, it should be apparent that those skilled in the art can make variations and modifications that will achieve some of the advantages of the invention without departing from the true scope of the invention. Accordingly, other embodiments are within the scope of the following claims.

What is claimed is:

1. A method of detecting polarized identification indicia in real-time using an image processor, the method comprising:
   providing from an image device a frame of image data having a plurality of pixels, wherein each pixel includes polarized light intensity information;
   determining, using the image processor, an intensity value for each of the pixels from the polarized light intensity information;
   selecting, using the image processor, a first portion of the pixels having intensity values within an intensity range;
   determining a degree of linear polarization value for each of the pixels in the first portion;
   and analyzing, using the image processor, the pixels in the first portion having similar angle of linear polarization values within a tolerance range, thereby detecting the polarized identification indicia in the image data.

2. The method of claim 1, further comprising:
   selecting a second portion of the pixels from the first portion, the second portion having degree of linear polarization values within a degree of linear polarization range.

3. The method of claim 1, wherein analyzing comprises gathering the pixels in the first portion into one or more groups, each group having similar angle of linear polarization values.

4. The method of claim 3, wherein analyzing comprises selecting the pixels having a distance from one another within a distance range for gathering into a group.

5. The method of claim 3, wherein analyzing comprises selecting groups having a size within a size range.

6. The method of claim 1, wherein the polarized light intensity information comprises horizontal linear polarization, vertical linear polarization and 45° degree linear polarization information with respect to a vertical viewing axis of an image device.

7. The method of claim 1, further comprising:
   highlighting the polarized identification indicia; and
   displaying the frame of image data with the highlighted polarized identification indicia overlaying the image data.

8. The method of claim 1, further comprising identifying the polarized identification indicia.

9. The method of claim 8, wherein identifying comprises:
   gathering the pixels in the first portion into one or more groups, each group having similar angle of linear polarization values;
   associating the one or more groups with corresponding code elements; and
   analyzing the code elements.

10. The method of claim 9, wherein analyzing the code elements comprises comparing the code elements to a database of polarization signatures.

11. The method of claim 1, wherein the frame of image data is provided from a stored video image or from a streaming video image.

12. A method of detecting polarized identification indicia in real-time using an image processor, the method comprising:
   providing from an image device a frame of image data having a plurality of pixels, wherein each pixel includes polarized light intensity information;
   determining, using the image processor, an intensity value for each of the pixels from the polarized light intensity information;
   selecting, using the image processor, a first portion of the pixels having intensity values within an intensity range;
   determining, using the image processor, a degree of linear polarization value for each of the pixels in the first portion;
   selecting, using the image processor, a second portion of the pixels from the first portion, the second portion having degree of linear polarization values within a degree of linear polarization range; and
   analyzing, using the image processor, the pixels in the second portion having similar angle of linear polarization values within a tolerance range, thereby detecting the polarized identification indicia in the image data.

13. The method of claim 12, wherein analyzing comprises gathering the pixels in the second portion into one or more groups, each group having similar angle of linear polarization values.

14. The method of claim 13, wherein analyzing comprises selecting the pixels having a distance from one another within a distance range for gathering into a group.

15. The method of claim 13, wherein analyzing comprises selecting groups having a size within a size range.

16. The method of claim 12, further comprising:
   highlighting the polarized identification indicia; and
   displaying the frame of image data with the highlighted polarized identification indicia overlaying the image data.

17. The method of claim 12, further comprising identifying the polarized identification indicia.

18. The method of claim 17, wherein identifying comprises:
   gathering the pixels in the second portion into one or more groups, each group having similar angle of linear polarization values;
   associating the one or more groups with corresponding code elements; and
   analyzing the code elements.

19. A computer program product, for use on a computer system, for detecting polarized identification indicia in real-time, the computer program product comprising a computer readable storage medium having computer readable program code stored thereon, the computer readable program code comprising:
   program code for determining an intensity value for image data having a plurality of pixels, wherein each pixel includes polarized light intensity information;
   program code for selecting a first portion of the pixels having intensity values within an intensity range;
   program code for determining a degree of linear polarization value for each of the pixels in the first portion; and
   program code for analyzing the pixels in the first portion having angle of linear polarization values within a tolerance range, thereby detecting the polarized identification indicia in the image data.

20. The computer program product of claim 19, wherein the computer readable program code further comprises:
   program code for selecting a second portion of the pixels from the first portion, the second portion having degree of linear polarization values within a degree of linear polarization range.

21. The computer program product of claim 19, wherein the computer readable program code for analyzing the pixels further comprises gathering the pixels in the first portion into one or more groups, each group having similar angle of linear polarization values.

22. The computer program product of claim 21, wherein the computer readable program code for analyzing the pixels further comprises selecting the pixels having a distance from one another within a distance range for gathering into a group.

23. The computer program product of claim 21, wherein the computer readable program code for analyzing the pixels further comprises selecting groups having a size within a size range.

24. The computer program product of claim 19, wherein the computer readable program code further comprises:
   program code for highlighting the polarized identification indicia; and
   program code for displaying the frame of image data with the highlighted polarized identification indicia overlaying the image data.

25. The computer program product of claim 19, wherein the computer readable program code further comprises identifying the polarized identification indicia.

26. The computer program product of claim 25, wherein the computer readable program code for identifying the polarized identification indicia further comprises:
   program code for gathering the pixels in the second portion into one or more groups, each group having similar angle of linear polarization values;
   program code for associating the one or more groups with corresponding code elements; and
   program code for analyzing the code elements.

27. A system of detecting polarized identification indicia in real-time comprising: an image device for receiving a frame of image data having a plurality of pixels, wherein each pixel includes polarized light intensity information; and
   an image processor configured to determine an intensity value for each of the pixels from the polarized light intensity information, to select a first portion of the pixels having intensity values within an intensity range, to determines a degree of linear polarization value for each of the pixels in the first portion and to analyze the pixels in the first portion having similar angle of linear polarization values within a tolerance range, thereby detecting the polarized identification indicia in the image data.

28. The system of claim 27, wherein the image processor further determines a degree of linear polarization value for each of the pixels in the first portion; and
   selects a second portion of the pixels from the first portion, the second portion having degree of linear polarization values within a degree of linear polarization range.

29. The system of claim 27, wherein analyze comprises gathering the pixels in the first portion into one or more groups, each group having similar angle of linear polarization values.

30. The system of claim 27, wherein the image processor further highlights the polarized identification indicia, the system further comprising:
   a display for displaying the frame of image data with the highlighted polarized identification indicia overlaying the image data.

31. The system of claim 27, wherein the image processor further identifies the polarized identification indicia.

32. The system of claim 31, wherein identifies comprises:
   gathering the pixels in the first portion into one or more groups, each group having similar angle of linear polarization values;
   associating the one or more groups with corresponding code elements; and
   analyzing the code elements.

* * * * *

UNITED STATES PATENT AND TRADEMARK OFFICE
CERTIFICATE OF CORRECTION

PATENT NO.           : 7,715,590 B2                                                                            Page 1 of 1
APPLICATION NO.  : 11/344971
DATED                    : May 11, 2010
INVENTOR(S)          : Sheila G. Whitaker It is certified that error appears in the above-identified patent and that said Letters Patent is hereby corrected as shown below:

Col. 10, claim 28, lines 10-11
delete "determines a degree of linear polarization value for each of the pixels in the first portion; and"

Signed and Sealed this

Sixth Day of July, 2010

David J. Kappos
*Director of the United States Patent and Trademark Office*